United States Patent [19]
Zanirato et al.
[11] Patent Number: 4,916,232
[45] Date of Patent: Apr. 10, 1990

[54] BIS-(1,2,3-TRIAZOL-1-YL)-DERIVATIVES

[75] Inventors: Paolo Zanirato; Francesco Pilati, both of Bologna; Antonio Chiolle, Ferrara, all of Italy

[73] Assignee: Ausimont S.p.A., Milan, Italy

[21] Appl. No.: 173,629

[22] Filed: Mar. 25, 1988

[30] Foreign Application Priority Data

Mar. 30, 1987 [IT] Italy .............................. 19897 A/87

[51] Int. Cl.[4] .......................................... C07D 249/06
[52] U.S. Cl. .................................................... 548/255
[58] Field of Search ........................................ 548/255

[56] References Cited

U.S. PATENT DOCUMENTS 3,161,651 12/1964 Stansburg, Jr. et al. ........... 548/255
3,324,085 6/1967 Horn .................................. 548/255

OTHER PUBLICATIONS

Singh et al., "Oxidative Ring-closure of bis, etc", Indian Journal of Chem. 8, (1970), pp. 514–517.

*Primary Examiner*—Glennon H. Hollrah
*Assistant Examiner*—Patricia L. Morris
*Attorney, Agent, or Firm*—Stevens, Davis, Miller & Mosher

[57] ABSTRACT

Bis-(1,2,3,triazol-1-yl)-derivatives of the following formula (I):

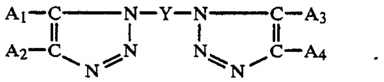

(I)

wherein Y is a bivalent radical selected from:

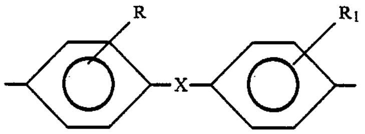

and

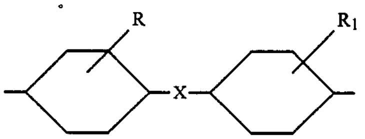

and X is a bivalent radical selected from —O—, —S—; $CR_2R_3$; $—NR_7—$; or an α-α′-alkylenedisubstituted cycloaliphaticketone.

10 Claims, No Drawings

BIS-(1,2,3-TRIAZOL-1-YL)-DERIVATIVES

BACKGROUND OF THE INVENTION

This invention relates to bis-(1,2,3-triazol-1-yl) derivatives, variously substituted in the pentatomic nucleus, as well as a method for their preparation.

The triazolyl derivatives and, in particular, the benzotriazoles, as well known from the literature. They are added, in general, to polymers in order to improve their physical-mechanical characteristics, and for improving their resistance to atmospheric agents.

These products, however, do not allow one to satisfy completely and exhaustively all of the requirements imposed by a practical application of a plastic material, especially when this latter is used for producing shaped articles to be used in the open air or in contact with a solvent. In fact, the benzotriazoles migrate towards the surface of the body and are easily extracted.

In accordance with the present invention, a new class of triazolic derivatives has now been discovered which do not show the above mentioned drawbacks.

DISCLOSURE OF THE INVENTION

In its wider aspect, the invention relates to a new class of bis-triazolyl-derivatives of the following formula (I):

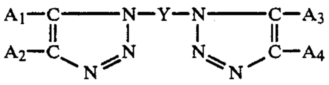
(I)

wherein:

Y is a bivalent radical selected from:

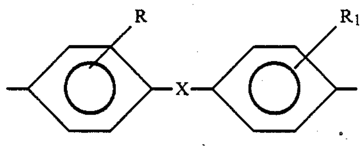

and

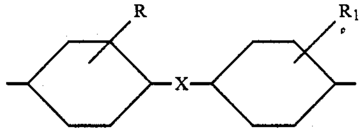

X is a bivalent radical selected from: —O—; —S—; $CR_2R_3$; $—NR_7—$ or an α-α'-alkylenesubstituted cycloaliphaticketone, wherein $R_2$, $R_3$ and $R_7$, equal to or different from each other, represent hydrogen or an alkyl group having from 1 to 18 carbon atoms;

R and $R_1$, equal to or different from each other, represent hydrogen or an alkyl group having from 1 to 4 carbon atoms; and $A_1$, $A_2$, $A_3$ and $A_4$, equal to or different from each other, are selected from:

(a) hydrogen;

(b) a $—COOR_4$ ester group, wherein $R_4$ may be hydrogen or an alkyl group having from 1 to 18 carbon atoms;

(c) a hydroxyalkyl $—(CH_2)_n—OH$ group, wherein n is zero or an integer between 1 and 18;

(d) an amino-alkyl—$(CH_2)_m—NR_5R_6$ group, wherein m is zero or an integer between 1 and 18, while $R_5$ and $R_6$, equal to or different from each other, represent hydrogen or an alkyl group having from 1 to 4 carbon atoms;

(e) a nitrile —CN group;

(f) an alkyl group having up to 18 carbon atoms, and (g) an aryl, arylalkyl or alkylaryl group having from 6 to 18 carbon atoms;

provided, however, that at least one of the $A_1$ or $A_2$ groups and at least one of the $A_3$ and $A_4$ groups are different from hydrogen and are selected from alkyl-, aryl-, arylalkyl-, or alkylaryl-groups.

The bis-triazolyl derivatives of formula (I) that are preferred in this invention are those in which:

Y is selected from diphenyl ether; diphenylmethane; diphenyl sulphide; 2,2-diphenyl propylene; 2,6-methylene-4-methyl cyclohexanone; and 2,5-propylene-cyclopentanone, and $A_1$, $A_2$, $A_3$ and $A_4$, equal to or different from each other, may be a $COOR_4$ ester group wherein $R_4$ represents hydrogen or an alkyl group having from 1 to 18 carbon atoms, a hydroxylalkyl $(—CH_2)_n—OH$ group wherein n is an integer between 1 and 4; a nitrile group or an aminoalkyl $(—CH_2)_m—NR_5R_6$ group in which m is an integer between 1 and 4 and where $R_5$ and $R_6$ represent hydrogen.

In the following, hereunder is given a list of triazolyl derivatives of the above reported formula (I), with no limiting purposes whatsoever:

(A)

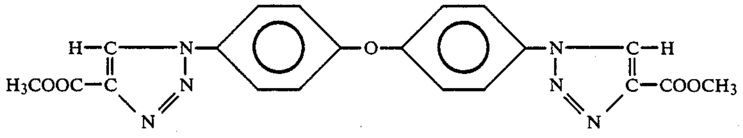

(B)

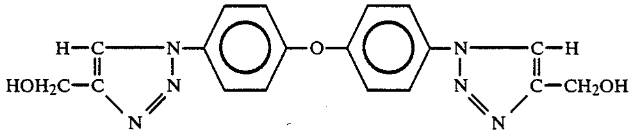

-continued (C)

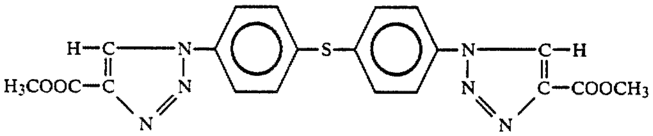

(D)

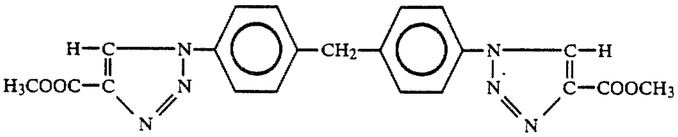

(E)

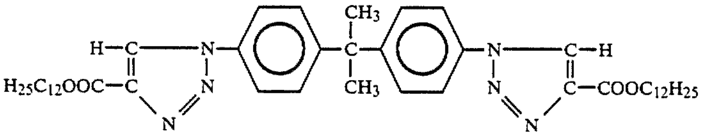

(F)

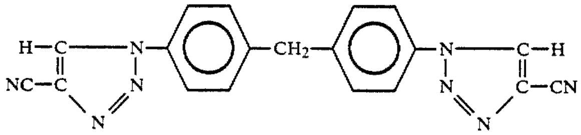

The bis-triazolyl derivatives of the formula (I) may be conveniently prepared following methods already described in the literature for the preparation of the mono-triazol derivatives.

wherein R, $R_1$ and X have the previously above indicated values; and then reacting the thus obtained diazonium chloride (III) with sodium azotide according to the scheme:

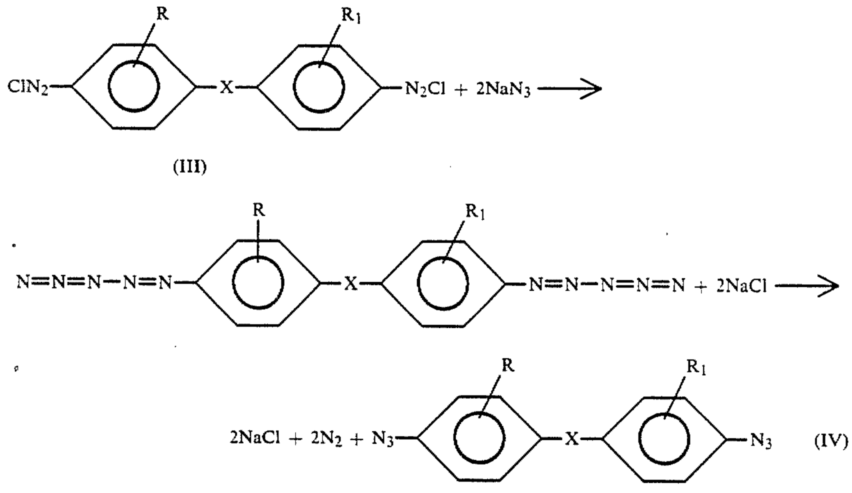

(III)

(IV)

Aliphatic diazides may be prepared by means of the nucleophile replacement of the halogen (bromine or chlorine) by the azidic group by refluxing for 24 hours a methanolic solution of alkyl dihalide in the presence of sodium azide.

A rather simple method that may be used in the preparation of aromatic diazides consists in effecting the diazotization (with $NaNO_2$ and HCl) of a diamine of the formula:

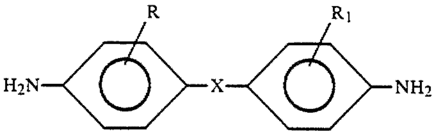

(II)

and successively by reacting the thus-obtained bis-azide (IV) with an acetylenic derivative according to the scheme:

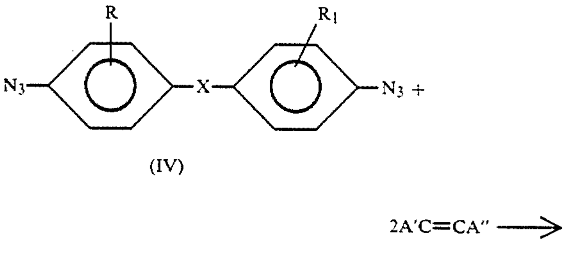

(IV)

(V)

(A′ and A″, equal to or different from each other, being $A_1$, $A_2$, $A_3$ or $A_4$).

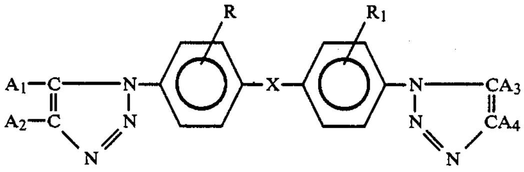

(VI)

When, for instance, one wishes to introduce into positions $A_2$ and $A_4$ an ester $-COOR_4$ radical, the bis-azidic (IV) compound is made to react with an alkyl ester of acetylene-carboxylic acid (propiolic acid).

The reaction between the bis-azide (IV) and the acetylenic compound (V) is preferably carried out in solution, such as for example in acetone, benzene or toluene, at a temperature between room temperature and the boiling point of the solvent.

The regio-selectivity of the reaction depends also on the solvent and on the temperature used during the reaction with the acetylene compound, and, in general, it increases with increasing polarity of the solvent. Thus, for instance, when the reaction is conducted with methyl-propiolate and at room temperature, in a benzenic solution, there are obtained mixtures of two isomers in the ratio 30:70, wherein the $-COOCH_3$ readical is respectively bound in the positions $A_1$–$A_3$ and $A_2$–$A_4$. On the other hand, by performing the same reaction in acetone, in a reflux condenser at about 70° C., the ratio between the two isomers will rise to 10:90.

The bis-triazolyl compounds of the present invention find their application both as additives for polymers, in order to improve their physical-mechanical characteristics and their resistance to atmospheric agents, as well as intermediates for the preparation of products of high molecular weight.

The examples given hereunder are meant for illustrative purposes only, and are not in any way limitative of the scope of the invention itself.

EXAMPLE 1

PART A (preparation of diazonium chloride)

0.1 moles of 4,4′-diaminodiphenyloxide, of formula:

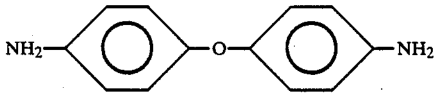

were introduced, together with 20 g of ice, into a glass flask fitted with a thermometer, a dripping funnel, and a magnetic stirrer, the flask being heat-stabilized at −15° C.

The diamine was additioned with 100 cm³ of a 67% by weight aqueous solution of HCl (without heating, and taking care to avoid the formation of lumps or clots) in order to form the hydrochloride. The temperature was then raised up to 0° C. and then there was added dropwise and under stirring 0.21 mole of $NaNO_2$, for the formation of the diazonium chloride. After about 90 minutes the reaction was practically complete and the end mixture showed up in the form of a clear solution.

PART B (formation of the diazide)

300 cm³ of water were introduced into a glass vessel of 1000 cm³ holding capacity, and then there were added 0.21 mole of sodium azide ($NaN_3$), 100 g of sodium acetate ($CH_3COONa$), and 200 g of ice. Thereupon there was dripped into the solution prepared in PART A containing the diazonium chloride, taking care that the temperature shall rise to 10° C. The reaction mechanism, as it is well known, is the following:

$$-RN_2Cl + NaN_3 \rightarrow -R-N=N-N=N=N- + NaCl \rightarrow -R-N_3 + N_2 + NaCl.$$

In these cases, sodium acetate acts as a buffer and allows one to avoid the formation of $HN_3$.

The reaction was finally completed, maintaining the reacting mixture at 7° C. overnight. The resulting mixture was then filtered under vacuum on a Buchner filter, the solid was recovered with ethyl ether and, after drying (on $Na_2SO_4$), the solvent was evaporated. A sample, obtained a second time by repeating the test, was diluted with normal-hexane in a silica gel column and the eluted product was used for determining the melting point of the diazide (T°=74°–75° C.).

PART C (formation of the 1,2,3-triazole ring)

The diazide (0.1 mole), obtained according to the method specified in PART B, was introduced into a thermostated glass flask fitted with a magnetic stirrer, having a holding capacity of 500 cm³ and containing 300 cm³ of acetone.

To this solution were then added 0.2 mole of the methyl ester of acetylene-carboxylic acid (propiolic acid) and the temperature was then raised up to 70° C., under continuous heating and mild stirring, under reflux conditions.

The reaction was carried out for a period of 3 days until there was noted (chromatographically) the disappearance of the original bis-azide.

After cooling down and after subsequent evaporation of acetone, there was obtained a white solid consisting of the mixture of the two isomers in the ratio of 80% (beta isomer) to 15% (alpha isomer).

The reaction (1,3-cyclo addition), in the case of carboxylic derivatives, may be in fact thus schematized:

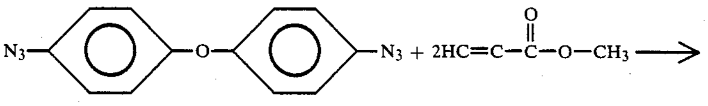

-continued

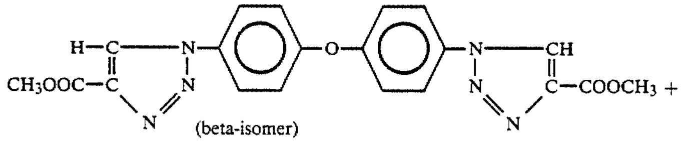

(beta-isomer)

The decomposition point of the mixture was 220° C. The beta-isomer was obtained in the pure state by means of crystallization from acetonitrile. The melting point of the beta-isomer was 230° C.

The formula of the beta-isomer was determined by I.R., NMR, and mass spectrophotometric analysis.

EXAMPLE 2

Example 1 was repeated in a substantially identical way, by replacing, in PART (C), the acetone by benzene and by carrying out the acetylenic cycloaddition of the same PART (C) at room temperature.

There was thus obtained a bis-triazolic mixture containing about 70% of the beta-isomer and about 30% of the alpha-isomer.

EXAMPLE 3

Example 1 was repeated in a substantially identical way, the diphenyloxide diamine being replaced by the corresponding diamine of diphenyl-methane. A mixture of alpha- and beta-isomers was obtained whose decomposition point was 250° C. The beta-isomer was obtained in the pure state by means of crystallization from acetonitrile. The melting point of the beta-isomer was 230° C.

The formula of the beta-isomer was determined by I.R., NMR, and mass spectrophotometric analysis.

What is claimed:

1. Bis-triazolyl derivatives of the formula:

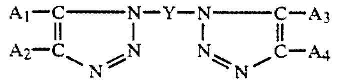

wherein:

Y is a bivalent radical selected from:

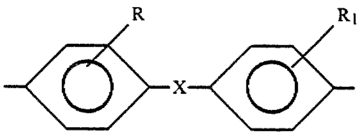

and

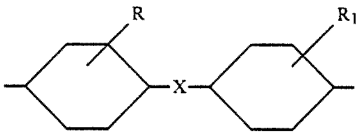

X is a bivalent radical selected from: —O—; —S—; $CR_2R_3$; —$NR_7$— and an aliphatic α-α'-alkylenesubstituted cycloketone, wherein $R_2$, $R_3$ and $R_7$, equal to or different from each other, represent hydrogen or an alkyl group having from 1 to 18 carbon atoms wherein the alkylene is a lower alkylene and the cycloketone is a cyclic hydrocarbon ketone having 4 to 10 carbon atoms;

R and $R_1$, equal to or different from each other, represent hydrogen or an alkyl group having from 1 to 4 carbon atoms; and $A_1$, $A_2$, $A_3$ and $A_4$, equal to or different from each other, are selected from:

(a) hydrogen;

(b) a —$COOR_4$ ester group, wherein $R_4$ may be hydrogen or an alkyl group having from 1 to 18 carbon atoms;

(c) a hydroxyalkyl —$(CH_2)_n$—OH group, wherein n is zero or an integer from 1 to 18;

(d) an amino-alkyl—$(CH_2)_m$—$NR_5R_6$ group, wherein m is zero or an integer from 1 to 18, while $R_5$ and $R_6$, equal to or different from each other, represent hydrogen or an alkyl group having from 1 to 4 carbon atoms;

(e) a nitrile —CN group;

(f) an alkyl group having up to 18 carbon atoms, and (g) an aryl, arylalkyl or alkylaryl group having from 6 to 18 carbon atoms;

provided, however, that at least one of the $A_1$ or $A_2$ groups and at least one of the $A_3$ and $A_4$ groups are different from hydrogen and selected from alkyl-, aryl-, arylalkyl- or alkylaryl- groups.

2. Bis-triazolyl derivatives according to claim 1, characterized in that:

Y is selected from the group consisting of ether; diphenyl methane; diphenyl sulphide; 2,2-diphenyl propylene; 2,6-dimethylene-4-methyl-cyclohexanone; 2,5-dipropylene-cyclopentanone;

$A_1$, $A_2$, $A_3$ and $A_4$, equal to or different from each other, may be a —$COOR_4$ ester group in which $R_4$ represents hydrogen or an alkyl group having from 1 to 18 carbon atoms; a hydroxy-alkyl (—$CH_2$-$)_n$—OH group in which n is an integer between 1 and 4; a nitrile group or an amino-alkyl —($CH_2$-$)_m$—$NR_5R_6$ group wherein m is an integer between 1 and 4, and where $R_5$ and $R_6$ represent hydrogen.

3. Bis-triazolyl derivative according to either claim 1 or claim 2, having the formula:

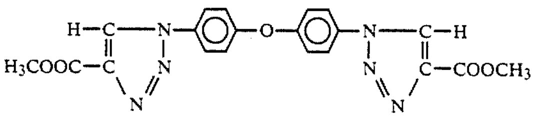

4. Bis-triazolyl derivative according to either claim 1 or claim 2, having the formula:

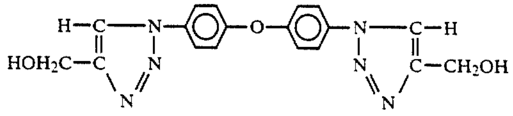

5. Bis-triazolyl derivative according to either claim 1 or claim 2, having the formula:

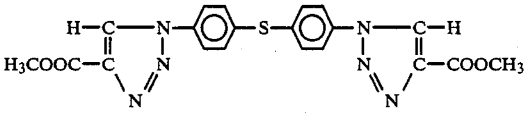

6. Bis-triazolyl derivative according to either claim 1 or claim 2, having the formula:

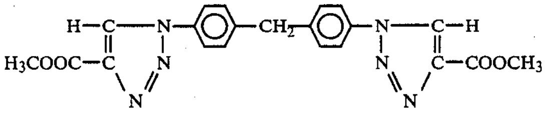

7. Bis-triazolyl derivative according to claim 1 or claim 2, having the formula:

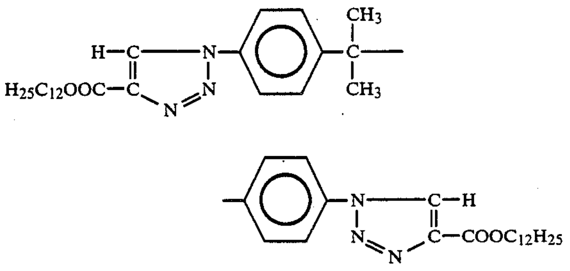

8. Bis-triazolyl derivative according to claim 1 or claim 2, having the formula:

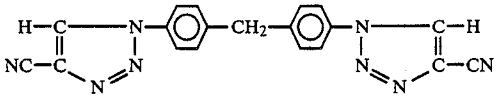

9. Bis-triazolyl derivative according to claim 1, wherein the α-α'-alkylene substituted cycloketone is 2,6-dialkylene-cycloaliphatic ketone wherein the alkylene groups have from 1 to 3 carbon atoms and the cycloaliphatic ring has from 5 to 6 carbon atoms.

10. Bis-triazolyl derivative according to claim 9, wherein the cycloaliphatic ring has 6 carbon atoms and bears one methyl group in the four position.

* * * * *